US00PP22696P2

(12) United States Plant Patent
Kolster et al.

(10) Patent No.: US PP22,696 P2
(45) Date of Patent: May 1, 2012

(54) ***HYDRANGEA* PLANT NAMED 'HOKOMANO'**

(50) Latin Name: *Hydrangea macrophylla*
Varietal Denomination: Hokomano

(75) Inventors: Peter R. Kolster, Boskoop (NL); Cornelis P. Eveleens, De Kwakel (NL)

(73) Assignee: Kolster Holding B.V., Boskoop (NL)

( * ) Notice: Subject to any disclaimer, the term of this patent is extended or adjusted under 35 U.S.C. 154(b) by 32 days.

(21) Appl. No.: 12/807,255

(22) Filed: Aug. 31, 2010

(51) Int. Cl.
*A01H 5/00* (2006.01)

(52) U.S. Cl. ..... Plt./250

(58) Field of Classification Search ..... Plt./250
See application file for complete search history.

*Primary Examiner* — June Hwu
(74) *Attorney, Agent, or Firm* — C. A. Whealy

(57) ABSTRACT

A new and distinct cultivar of *Hydrangea* plant named 'Hokomano', characterized by its broadly upright plant habit; strong erect stems; freely flowering habit; and globular mophead-type inflorescences with white-colored sterile flowers with green-colored margins and red purple-colored centers.

3 Drawing Sheets

Botanical designation: *Hydrangea macrophylla.*
Cultivar denomination: 'HOKOMANO'.

BACKGROUND OF THE INVENTION

The present invention relates to a new and distinct cultivar of *Hydrangea* plant, botanically known as *Hydrangea macrophylla* and hereinafter referred to by the name 'Hokomano'.

The new *Hydrangea* plant is a naturally-occurring whole plant mutation of *Hydrangea macrophylla* 'Magical Emerald' (U.S. Plant Pat. No. 20,464). The new *Hydrangea* plant was discovered and selected by the Inventors as a single flowering plant from within a population of plants of 'Magical Emerald' in a controlled greenhouse environment in Boskoop, The Netherlands in July, 2007.

Asexual reproduction of the new *Hydrangea* plant by vegetative cuttings in a controlled greenhouse environment in Boskoop, The Netherlands since August, 2007, has shown that the unique features of this new *Hydrangea* plant are stable and reproduced true to type in successive generations.

SUMMARY OF THE INVENTION

Plants of the new *Hydrangea* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Hokomano'. These characteristics in combination distinguish 'Hokomano' as a new and distinct *Hydrangea* plant:

1. Broadly upright plant habit.
2. Strong erect stems.
3. Freely flowering habit.
4. Globular mophead-type inflorescences with white-colored sterile flowers with green-colored margins and red purple-colored centers.

Plants of the new *Hydrangea* differ from plants of the parent, 'Magical Emerald', primarily in flower color as plants of 'Hulk' have pink-colored sterile flowers.

Plants of the new *Hydrangea* can be compared to plants of *Hydrangea* 'Snowball', not patented. Plants of the new *Hydrangea* differ primarily from plants of 'Snowball' in the following characteristics:

1. Plants of the new *Hydrangea* have shorter lateral branches than plants of 'Snowball'.
2. Plants of the new *Hydrangea* and 'Snowball' differ in flower color as plants of 'Snowball' have white-colored sterile flowers.

Plants of the new *Hydrangea* can also be compared to plants of *Hydrangea* 'Magical Pearl', disclosed in U.S. Plant Pat. No. 20,614. Plants of the new *Hydrangea* differ primarily from plants of 'Magical Pearl' in the following characteristics:

1. Plants of the new *Hydrangea* have longer lateral branches than plants of 'Magical Pearl'.
2. Plants of the new *Hydrangea* and 'Magical Pearl' differ in flower color as plants of 'Magical Pearl' have light green to white-colored sterile flowers.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color value cited in the detailed botanical description which accurately describe the colors of the new *Hydrangea* plant.

The photograph on the first sheet comprises a side perspective view of a typical plant of 'Hokomano' grown in a container.

The photograph on the second sheet is a close-up view of a typical leaf of 'Hokomano'.

The photograph on the third is a close-up view of a typical inflorescence of 'Hokomano'.

DETAILED BOTANICAL DESCRIPTION

Plants used in the aforementioned photographs and in the following description were grown during the spring in 19-cm containers in a glass-covered greenhouse in Boskoop, The Netherlands under conditions which closely approximate commercial production conditions. During the production of the plants, day temperatures ranged from 18° C. to 25° C. and night temperatures ranged from 10° C. to 17° C. Plants of the new *Hydrangea* were two years old when the photographs and description were taken. In the following description, color references are made to The Royal Horticultural Society Colour Chart, 2007 Edition, except where general terms of ordinary dictionary significance are used.

Botanical description: *Hydrangea macrophylla* 'Hokomano'.

Parentage: Naturally-occurring whole plant mutation of *Hydrangea macrophylla* 'Magical Emerald' (U.S. Plant Pat. No. 20,464).

Propagation:

*Method*.—By softwood cuttings.

*Time to initiate roots, summer*.—About three weeks at temperatures of 15° C. to 25° C.

*Time to initiate roots, winter*.—About five weeks at temperatures of 10° C. to 20° C.

*Time to produce a rooted young plant, summer*.—About six weeks at temperatures of 15° C. to 25° C.

*Time to produce a rooted young plant, winter*.—About ten weeks at temperatures of 10° C. to 20° C.

*Root description*.—Medium in thickness, fibrous; cream in color.

*Rooting habit*.—Moderately branching; medium in density.

Plant description:

*Form/growth habit*.—Upright plant habit; broad inverted triangle; strong erect stems; about eleven lateral branches develop per plant, pinching enhances lateral branch development; moderately vigorous growth habit.

*Plant height*.—About 53.8 cm.

*Plant diameter or area of spread*.—About 72.5 cm.

*Lateral branches*.—Length: About 31.9 cm. Diameter: About 6 mm. Internode length: About 9.6 cm. Texture, developing and fully developed: Smooth, glabrous. Angle: Mostly erect to about 45° from vertical. Strength: Strong. Color, developing: Close to 143C. Color, fully developed: Close to 199B and N199B.

Foliage description:

*Arrangement*.—Opposite, simple.

*Length*.—About 11.7 cm.

*Width*.—About 9 cm.

*Shape*.—Broadly elliptic to oblong.

*Apex*.—Broadly apiculate.

*Base*.—Rounded to attenuate.

*Margin*.—Serrate.

*Texture, upper surface*.—Smooth, glabrous; slightly rugose.

*Texture, lower surface*.—Smooth, glabrous.

*Venation pattern*.—Pinnate.

*Color*.—Developing leaves, upper surface: Close to N137C. Developing leaves, lower surface: Close to 147B. Fully expanded leaves, upper surface: Close to N137B to N137C; venation, close to 145C. Fully expanded leaves, lower surface: Close to 147B; venation, close to 145B.

*Petiole*.—Length: About 3.3 cm. Diameter: About 4 mm Texture, upper and lower surfaces: Smooth, glabrous. Color, upper and lower surfaces: Close to 145B.

Flower description:

*Flower type and habit*.—Single fertile and sterile flowers arranged on terminal mophead-type panicles; panicles globular; sterile flowers face upright to outwardly and fertile flowers face upright.

*Fragrance*.—None detected.

*Natural flowering season*.—Continuous flowering from late spring to late summer in The Netherlands.

*Flower longevity*.—Sterile flowers last about six weeks on the plant; sterile flowers persistent; fertile flowers last about one week on the plant; fertile flowers not persistent.

*Quantity of flowers*.—Freely flowering habit; about 35 fertile flowers and about 125 sterile flowers per panicle.

*Panicle height*.—About 11.2 cm.

*Panicle diameter*.—About 18 cm.

*Flower buds, fertile flowers*.—Length: About 4 mm. Diameter: About 4 mm. Shape: Broadly obovate. Color: Close to N144C.

*Flower buds, sterile flowers*.—Length: About 8 mm. Diameter: About 7 mm. Shape: Obovate. Color: Close to 145C to 145D.

*Fertile flowers*.—Diameter: About 6 mm. Depth: About 6 mm. Shape: Rotate, campanulate. Petals: Quantity: Four. Length: About 3 mm. Width: About 2.5 mm. Shape: Elliptic. Apex: Acute. Base: Cuneate. Margin: Entire. Texture, upper and lower surfaces: Smooth, glabrous. Color: When opening, upper and lower surfaces: Close to 143B; towards the base, close to 65D. Fully opened, upper and lower surfaces: Close to 143B; towards the base, close to 65D. Sepals: Quantity: Five. Length: About 2.5 mm. Width: About 1.2 mm. Shape: Ovate. Apex: Acute. Base: Fused. Margin: Entire. Texture, upper and lower surfaces: Smooth, glabrous. Color: When opening, upper and lower surfaces: Close to 145C. Fully opened, upper and lower surfaces: Close to 145C. Pedicels: Length: About 5 mm. Diameter: About 1 mm. Strength: Moderately strong. Angle: About 10° from vertical. Texture: Smooth, glabrous. Color: Close to 68D tinged with close to 145C. Reproductive organs: Stamens: Quantity per flower: Eight. Filament length: About 4 mm. Filament color: Close to 68D and 69A. Anther shape: Broadly reniform. Anther length: About 0.75 mm. Anther color: Close to 156D. Pollen amount: Moderate. Pollen color: Close to 155A. Pistils: Quantity per flower: Three. Pistil length: About 1 mm. Stigma shape: Club-shaped. Stigma color: Close to 145B to 145C tinged with close to 69A. Style length: About 0.6 mm. Style color: Close to 145B to 145C tinged with close to 68D. Ovary color: Close to 145C to 145D.

*Sterile flowers*.—Shape: Rotate. Diameter: About 4.9 cm. Depth (height): About 1.5 cm. Petals: Quantity: Four. Length: About 5 mm. Width: About 2.5 mm. Shape: Elliptic. Apex: Acute. Base: Cuneate. Margin: Entire. Texture, upper and lower surfaces: Smooth, glabrous. Color: When opening, upper surface: Close to 72D and 73A. When opening, lower surface: Close to 73B. Fully opened, upper and lower surfaces: Close to 75C. Sepals: Quantity: Four. Length: About 2.7 cm. Width: About 3 cm. Shape: Broadly deltoid to broadly rhomboidal or orbicular. Apex: Broadly to bluntly acute. Base: Cuneate. Margin: Serrate. Texture, upper and lower surfaces: Smooth, glabrous. Color: When opening, upper surface: Close to 69C to 69D. When opening, lower surface: Close to 69D and N155B.

Fully opened, upper surface: Close to 67A to 67B, apex close to 146D; with development, close to NN155C to NN155D, towards the apex, close to 145B. Fully opened, lower surface: Close to 75B to 75C tinged with close to 145B to 145C; with development, close to NN155C to NN155D, towards the apex, close to 145B. Pedicels: Length: About 2.8 cm. Diameter: About 2 mm Strength: Strong. Angle: About 30° from vertical. Texture: Pubescent. Color: Close to 68C. Reproductive organs: Stamens: Quantity per flower: Eight. Filament length: About 3 mm. Filament color: Close to 72C to 72D. Anther shape: Broadly reniform. Anther length: About 0.75 mm Anther color: Close to 156D. Pollen amount: Moderate. Pollen color: Close to 155A. Pistils: Quantity per flower: Three. Pistil length: About 1 mm. Stigma shape: Club-shaped. Stigma color: Close to 187B. Style length: About 0.6 mm. Style color: Close to 72C to 72D. Ovary color: Close to 72D and 73A.

*Fruits/seeds*.—Fruit and seed development have not been observed on plants of the new *Hydrangea*.

Disease/pest resistance:

Plants of the new *Hydrangea* have not been observed to be resistant to pathogens or pests common to *Hydrangea*.

Temperature tolerance:

Plants of the new *Hydrangea* have been shown to be tolerant to temperatures ranging from about −20° C. to about 40° C.

It is claimed:

1. A new and distinct *Hydrangea* plant named 'Hokomano' as illustrated and described.

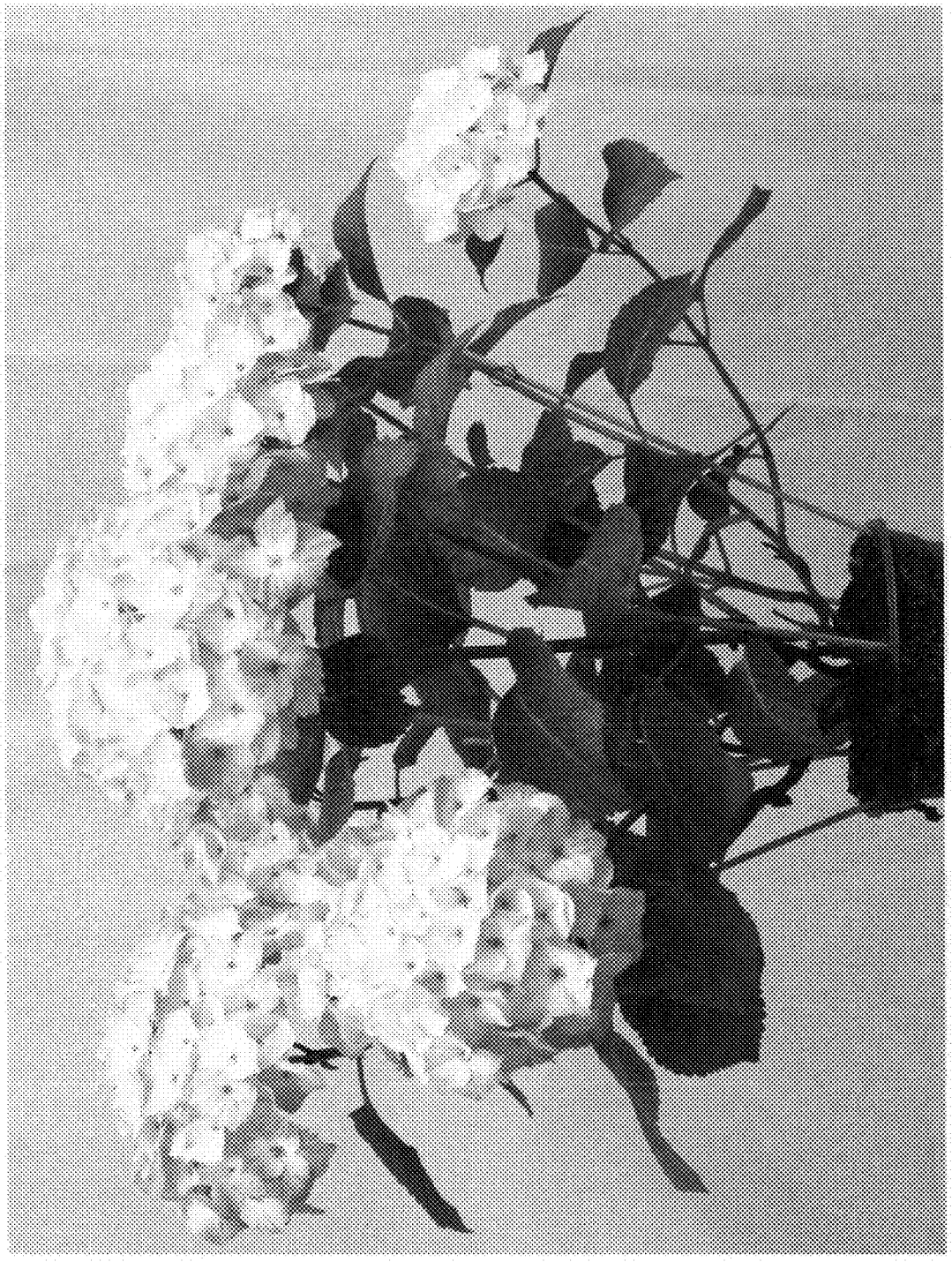

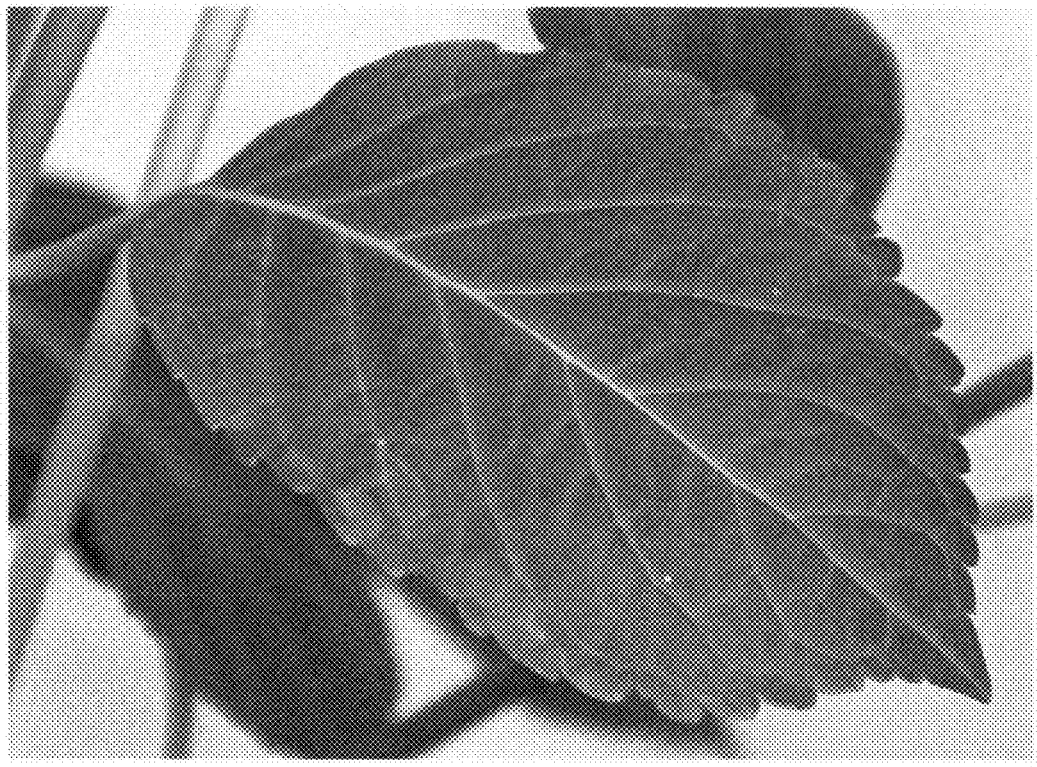

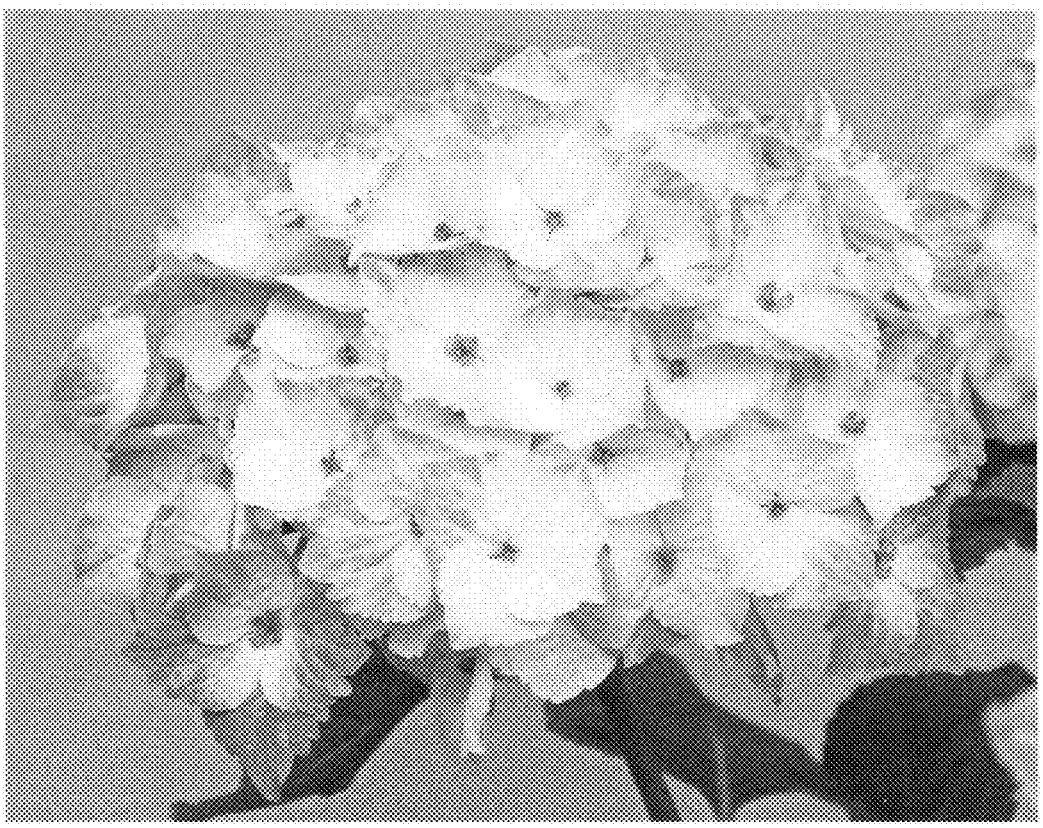

* * * * *